US009782362B2

(12) United States Patent
Back et al.

(10) Patent No.: US 9,782,362 B2
(45) Date of Patent: Oct. 10, 2017

(54) USES OF COMPOSITIONS CONTAINING A ROASTED EXTRACT AND XANTHOHUMOL

(71) Applicant: TA-XAN AG, Wiesbaden (DE)

(72) Inventors: Werner Back, Freising (DE); Achim Zuercher, Riehen (CH); Sascha Wunderlich, Freising (DE)

(73) Assignee: TA-XAN AG, Wiesbaden (DE)

( * ) Notice: Subject to any disclaimer, the term of this patent is extended or adjusted under 35 U.S.C. 154(b) by 0 days.

(21) Appl. No.: 14/417,193

(22) PCT Filed: Jul. 26, 2013

(86) PCT No.: PCT/EP2013/065804
§ 371 (c)(1),
(2) Date: Jan. 26, 2015

(87) PCT Pub. No.: WO2014/016409
PCT Pub. Date: Jan. 30, 2014

(65) Prior Publication Data
US 2015/0246008 A1    Sep. 3, 2015

(30) Foreign Application Priority Data
Jul. 26, 2012   (DE) .................. 10 2012 014 745

(51) Int. Cl.
A61K 36/00       (2006.01)
A61K 31/12       (2006.01)
A61K 36/185      (2006.01)
A61K 36/899      (2006.01)

(52) U.S. Cl.
CPC ............ A61K 31/12 (2013.01); A61K 36/185 (2013.01); A61K 36/899 (2013.01)

(58) Field of Classification Search
None
See application file for complete search history.

(56) References Cited

U.S. PATENT DOCUMENTS

| | | | |
|---|---|---|---|
| 5,679,716 A | 10/1997 | Tobe et al. | |
| 6,867,332 B1 | 3/2005 | Biendl et al. | |
| 7,736,677 B2 | 6/2010 | Tripp et al. | |
| 8,003,135 B2 | 8/2011 | Back et al. | |
| 8,303,999 B2 | 11/2012 | Back et al. | |
| 2004/0121040 A1 | 6/2004 | Forster et al. | |
| 2007/0059393 A1 | 3/2007 | Tajima et al. | |
| 2008/0008776 A1* | 1/2008 | Back et al. | 424/778 |
| 2008/0051465 A1 | 2/2008 | Tripp et al. | |
| 2009/0124703 A1 | 5/2009 | Ono et al. | |
| 2009/0209654 A1 | 8/2009 | Kuhrts | |
| 2010/0029757 A1 | 2/2010 | Hellerbrand | |
| 2011/0021637 A1 | 1/2011 | Tripp et al. | |
| 2011/0086815 A1* | 4/2011 | Yamaguchi ........... A23L 1/3002 514/58 |
| 2011/0280968 A1 | 11/2011 | Back et al. | |

FOREIGN PATENT DOCUMENTS

| | | |
|---|---|---|
| DE | 19939350 A1 | 2/2001 |
| DE | 10240065 A1 | 3/2004 |
| DE | 10256166 A1 | 6/2004 |
| DE | 10256031 A1 | 6/2005 |
| DE | 102006062264 A1 | 6/2008 |
| EP | 0679393 A2 | 11/1995 |
| EP | 1431385 A1 | 6/2004 |
| JP | 2006306800 A | 11/2006 |
| JP | 2008524299 A | 7/2008 |
| JP | 2008532558 A | 8/2008 |
| JP | 2009502973 A | 1/2009 |
| JP | 2010513360 A | 4/2010 |
| JP | 2010536772 A | 12/2010 |
| WO | 2004089359 A1 | 10/2004 |
| WO | 2006066941 A2 | 6/2006 |

OTHER PUBLICATIONS

Wunderlich, Enrichment of xanthohumol in the brewing process. Molecular nutrition & food research, (Sep. 2005) vol. 49, No. 9, pp. 874-81.*

Masic, Socio-medical Characteristics of Coronary Disease in Bosniaand Herzegovina and the World. Materia socio-medica, (2011) vol. 23, No. 3, pp. 171-183.*

Viljoen, Safety and efficacy of laropiprant and extended-release niacin combination in the management of mixed dyslipidemias and primary hypercholesterolemia. Drug, Healthcare and Patient Safety, (2010) vol. 2, No. 1, pp. 61-71.*

(Continued)

Primary Examiner — Qiuwen Mi
(74) Attorney, Agent, or Firm — Abel Law Group, LLP

(57) ABSTRACT

The present invention primarily relates to specific uses of a composition containing a roasted extract and xanthohumol for health-promoting purposes. In particular, the invention relates to a composition, preferably pharmaceutical composition, comprising xanthohumol (XN), preferably in a therapeutically effective amount, for (i) use in the treatment and/or prevention of cancer, and/or (ii) use in the treatment and/or prevention of osteoporosis, and/or (iii) use in the treatment and/or prevention of metabolic syndrome, and/or (iv) use in the treatment and/or prevention of diabetes, and/or (v) use in the treatment and/or prevention of cardiovascular disease(s), and/or (vi) use as anti-oxidant, and/or (vii) use as detoxifying agent, and/or (viii) inhibiting metabolic activation of procarcinogens, and/or (ix) use as anti-mutagenic and/or anti-genotoxic agent, and/or (x) use as anti-estrogenic and/or estrogenic agent, and/or (xi) inducing apoptosis, and/or (xii) use as anti-angiogenetic agent, and/or (xiii) use as anti-inflammatory agent, and/or (xiv) inhibiting NF-κB, and/or (xv) use in the treatment and/or prevention of infection(s), in particular, use as antimicrobial agent, wherein the composition comprises or consists of (a) a roasted extract and (b) XN, preferably a hop extract comprising XN, and/or wherein the composition is obtainable or obtained by mixing (a) a roasted extract and (b) XN or, preferably, a hop extract comprising XN.

20 Claims, No Drawings

(56) References Cited

OTHER PUBLICATIONS

Jezer, Work capacity of the cardiac. Medical Clinics of North America, (1953) vol. 37, No. 3.*

Tual-Chalot et al, Endothelial depletion of Acvrl1 in mice leads to arteriovenous malformations associated with reduced endoglin expression. PloS one, (2014) vol. 9, No. 6, pp. e98646. Electronic Publication Date: Jun 4, 2014.*

Vrachnis, Impact of maternal diabetes on epigenetic modifications leading to diseases in the offspring. Experimental diabetes research, (2012) vol. 2012, pp. 538474.*

Biala et al, Mitochondrial dynamics: Orchestrating the journey to advanced age. Journal of molecular and cellular cardiology, (Jun. 2015) vol. 83, pp. 37-43.*

* cited by examiner

USES OF COMPOSITIONS CONTAINING A ROASTED EXTRACT AND XANTHOHUMOL

BACKGROUND OF THE INVENTION

1. Field of the Invention

The present invention primarily relates to specific uses of a composition containing a roasted extract and xanthohumol for health-promoting purposes.

2. Discussion of Background Information

It is well known that xanthohumol has very diverse positive effects on human and animal health. For example, besides antimicrobial effects, preventive activity against a wide range of diseases by various mechanisms is being observed.

For example, cancer-preventive activity, protective action against osteoporosis, metabolic syndrome, diabetes and cardiovascular diseases have been reported.

It should be mentioned that these sub-divisions cannot be stringent. For example, anti-oxidative effects are just as positive in the prevention of tumors as, for example, with the metabolic syndrome or other diseases that up to now have not been investigated in connection with xanthohumol.

A large number of studies describes cancer-preventing mechanisms and were conducted in vitro, mostly in cell culture. Separate reference is made to the in vivo tests. The genesis of a tumor is a multi-factorial phenomenon; many mechanisms work interactively, many are known, many unknown. A frequently applied classification summarizes the early molecular events as "tumor initiation", the mechanisms of the development and establishment of a tumor as "tumor promotion" and the growth of a tumor as "tumor progression". The effect of xanthohumol was examined in a wide diversity of systems in line with the many mechanisms; these have been summarized and described as follows.

Phase I enzymes denote the enzymes that are responsible for the metabolic transformation of pro-carcinogenic substances into reactive carcinogenic metabolites, i.e. toxification. The inhibition of such enzymes by xanthohumol in tumor cells in culture, in rat liver and in recombinant human enzyme has been described by Henderson et al. (2000), *Xenobiotica*, 30, 235-251; Miranda et al. (2000), *Cancer Lett.*, 149, 21-29; Miranda et al. (2000), *Drug Metab Dispos.*, 28, 1297-1302 and Gerhauser et al. (2002), *Mol. Cancer Ther.*, 1, 959-969.

Phase II enzymes are those which are responsible in the organism for the conjugation of reactive, carcinogenic metabolites, secreting them from the cells towards detoxification. The stimulation of this class of enzyme is hence protective. Stimulation by way of xanthohumol in human liver tumor culture cells has also been described by Henderson et al. (2000), *Xenobiotica*, 30, 235-251; Miranda et al. (2000), *Cancer Lett.*, 149, 21-29; Miranda et al. (2000), *Drug Metab Dispos.*, 28, 1297-1302 and Gerhauser et al. (2002), *Mol. Cancer Ther.*, 1, 959-969.

Cellular oxidation is a process necessary to the organism to maintain life (securing of energy, respiration, bacterial defense). During its course, oxidative damage is caused that the healthy organism will eliminate using its own repair systems. If these systems are inadequate, whether because of defects, because of an excess of oxidative injury, as for example with chronic inflammations, reactive, oxidative molecules can react with the body's own macromolecules and lead to defects and mutation that may be the cause of a tumor as well as of other diseases. For this reason, anti-oxidative characteristics are highly significant for the prevention of tumors and other cellular injuries. Xanthohumol inhibits the formation and the action of reactive oxygen and hydrogen molecules in cell cultures, in rat liver fractions and in enzymatic model systems, as described by Miranda et al. (2000), *J. Agric. Food Chem.*, 48, 3876-3884; Rodriguez et al. (2001), *Food Chem. Toxicol.*, 39, 437-445; Gerhauser et al. (2002), *Mol. Cancer Ther.*, 1, 959-969, Stevens et al. (2003) *Chem. Res. Toxicol.*, 16, 1277-1286 and Vogel et al. (2008), Natural and non-natural prenylated chalcones: Synthesis, cytotoxicity and anti-oxidative activity. *Bioorg. Med. Chem.*, e-pub. It should be said that xanthohumol is not able to intercept the stable diphenylpicrylhydrazyl (DPPH) radical in direct chemical interaction (Gerhauser et al. (2002), *Mol. Cancer Ther.*, 1, 959-969; Dietz et al. (2005), *Chem Res. Taxieal.*, 18, 1296-1305; Gerhauser and Frank (2005), *Mol. Nutr. Food Res.*, 49, 821823; Jung et al. (2005), *Arch. Pharm Res.*, 28, 534-540). It would appear that the antioxidative effect of xanthohumol is derived from indirect cellular mechanisms.

As already described, inflammatory processes are often the cause of the formation of oxidative noxious substances that may be responsible for a number of diseases. Not only this, substances are detected in many human tumors that indicate the involvement of inflammatory processes. For this reason, anti-inflammatory agents act preventively against tumors. In Gerhauser et al. (2002), *Mol. Cancer Ther.*, 1, 959-969; Zhao et al. (2003), *Biol Pharm. Bull.*, 26, 61-65 and Cho et al. (2008), *Int. Immunopharmacol.*, 8, 567-573, xanthohumol is described in cell culture as being anti-inflammatory; in Monteiro et al. (2008) Xanthohumol inhibits inflammatory factor production and angiogenesis in breast cancer xenografts, *J. Cell Biochem*, e-pub, the inhibitive effect on inflammation was also established in vivo in mice after the oral administration of a dose of 4-6 mg/kg per day for 60 days in drinking water.

Estrogen is a growth factor and provides degenerate cells with an edge on growth. For this reason, anti-estrogens are considered to have a cancer-preventive action with tumors that depend on hormones. In Gerhauser et al. (2002), *Mol. Cancer Ther.*, 1, 959-969; Effenberger et al. (2005), *J. Steroid Biochem. Mol. Biol.*, 96, 387-399; Monteiro et al. (2006), *J. Agric. Food Chem.*, 54, 2938-2943 and Monteiro et al. (2007) *J. Steroid Biochem. Mol. Biol.*, 105, 124130, the anti-estrogen effect of Xanthohumol in vitro has been described; this is also described in Gerhauser et al. (2002), *Mol. Cancer Ther.*, 1, 959-969 in an organ culture model of the mouse mammary gland. In an in vivo test on rats, it was also possible to detect anti-estrogen action after the oral application of three×100 mg/kg xanthohumol over three days (Gerhauser and Frank (2005), *Mol. Nutr. Food Res.*, 49, 821823).

A significant feature in the genesis and growth of a tumor is the pronounced growth of the tumor cells. Inhibition of proliferation serves to prevent cancer and to provide tumor therapy. For this reason anti-proliferative substances are sought that inhibit the growth of tumor cells, yet at the same time do not destroy healthy cells. In many cases, of course, this is a question of dose and the onset time of substance action. Xanthohumol has been described as inhibiting growth in 24 different tumor cell lines (Miranda et al. (1999), *Food Chem. Toxicol.*, 37, 271-285; Gerhauser et al. (2002), *Mol. Cancer Ther.*, 1, 959-969; Herath et al. (2003), *Chem Pharm. Bull.* (Tokyo), 51, 1237-1240; Dietz et al. (2005), *Chem Res. Taxieal.*, 18, 1296-1305; Goto et al. (2005), *Cancer Lett.*, 219, 215-222; Lust et al. (2005), *Mol. Nutr. Food Res.*, 49, 844850; Pan et al. (2005), *Mol. Nutr. Food Res.*, 49, 837-843; Albini et al. (2006), *FASEB J.*, 20, 527-529; Oelmulle et al. (2006), *Phytomedicine.*, 13, 732-

734; Colgate et al. (2007), *Cancer Lett.*, 246, 201-209; Dell'Eva et al. (2007), *Cancer*, 110, 2007-2011; Lee et al. (2007), *Arch Pharrn. Res.*, 30, 14351439; Monteiro et al. (2007), *J. Steroid Biochem. Mol. Biol.*, 105, 124130; Delmulle et al. (2008), *Phytother Res.*, 22, 197-203; Monteiro et al. (2008), Xanthohumol inhibits inflammatory factor production and angiogenesis in breast cancer xenografts, *J. Cell Biochem*, e-pub and Vogel et al. (2008) Natural and non-natural prenylated chalcones: Synthesis, cytotoxicity and anti-oxidative activity, *Bioorg. Med. Chem*, e-pub).

Apoptosis is an ambivalent phenomenon and in healthy tissue is considered to be damaging. It is, however, desirable for the removal of damaged cells and cancer cells. Hence apoptosis-inducing substances can be both cancer-preventive and therapeutic. The induction of apoptosis by xanthohumol could be detected in cell cultures (Gerhauser and Frank (2005), *Mol. Nutr. Food Res.*, 49, 821823; Lust et al. (2005), *Mol. Nutr. Food Res.*, 49, 844850; Pan et al. (2005), *Mol. Nutr. Food Res.*, 49, 837-843; Vanhoecke (2005), *Int. J Cancer*, 117, 889-895; Colgate et al. (2007), *Cancer Lett.*, 246, 201-209; Dell'Eva et al. (2007), *Cancer*, 110, 2007-2011; Yang et al. (2007), *Apoptosis.*, 12, 1953-1963) and in vivo in mice (Monteiro et al. (2008) Xanthohumol inhibits inflammatory factor production and angiogenesis in breast cancer xenografts, *J. Cell Biochem.*, e-pub) after 4-6 mg/kg per day for 60 days in the drinking water.

To grow, a tumor needs to be supplied with nutrients. Once it has reached a certain size, new blood vessels are formed for this purpose, without which the tumor's growth would stagnate. Hence angiogenesis inhibitors act to prevent cancer and are effective in cancer therapy. The anti-angiogenetic action of xanthohumol is described in cell culture (Gerhauser and Frank (2005), *Mol. Nutr. Food Res.*, 49, 821823; Albini et al. (2006), *FASEB J.*, 20, 527-529; Dell'Eva et al., *Cancer*, 110, 2007-2011) and in vivo in mice (Gerhauser and Frank (2005), *Mol. Nutr. Food Res.*, 49, 821823; Albini et al. (2006), *FASEB J.*, 20, 527-529; Monteiro et al. (2008), Xanthohumol inhibits inflammatory factor production and angiogenesis in breast cancer xenografts, *J. Cell Biochem.*, e-pub) after doses of approx. 1 mg/kg per day (Albini et al. (2006), *FASEB J.*, 20, 527-529) for three days per os, 4-6 mg/kg per day for 60 days in drinking water (Monteiro et al. (2008), *J. Cell Biochem.*, e-pub) or 1000 mg/kg subcutaneously (Gerhauser and Frank (2005), *Mol. Nutr. Food Res.*, 49, 821823).

In further studies on molecular mechanisms in the protective action of xanthohumol, the influence on the NF-κB (nuclear factor kappa B) was noted. NF-κB is a cellular transcription factor that plays a part in the stimulation and production of pro-inflammatory target genes such as interleukin, tumor necrosis factor α, inducible nitric oxide synthase (iNOS), and inducible cyclooxigenase (Cox-2) and has a determinant influence on progression and duration of an inflammation. The diseases featuring NF-κB-regulated genes include inflammatory events with glomerulonephritis, arteriosclerosis, septic shock or pulmonary fibrosis, as well as chronic diseases such as asthma and rheumatoid arthritis. In Albini et al. (2006), *FASEB J.*, 20, 527-529; Colgate (2007), *Cancer Lett.*, 246, 201-209; Dell'Eva et al. (2007), *Cancer*, 110, 2007-2011 and Monteiro et al. (2008), *J. Cell Biochem.*, e-pub, the inhibition of the NF-κB is described in cell culture and in vivo.

In animal studies, xanthohumol was investigated for its action in preventing cancer. It could be demonstrated that in three different tumor models, xanthohumol inhibited formation of the tumor. Human breast tumor cells (MX-1 cells in the study Gerhauser and Frank (2005), *Mol. Nutr. Food Res.*, 49, 821823; MXF7 cells in the study Monteiro et al. (2008), Xanthohumol inhibits inflammatory factor production and angiogenesis in breast cancer xenografts, *J. Cell Biochem.*, e-pub) were transferred to immune-deficient mice and the growth of the tumor measured. As described in Gerhauser and Frank (2005), *Mol. Nutr. Food Res.*, 49, 821823, following a daily subcutaneous administration of 1000 mg/kg xanthohumol, the growth of the tumor was inhibited by 46% in one week and by 83% in two weeks. As described in Monteiro et al. (2008), Xanthohumol inhibits inflammatory factor production and angiogenesis in breast cancer xenografts, *J. Cell Biochem.*, e-pub, with a daily dose of 4-6 mg/kg xanthohumol in the drinking water, the growth of the tumor was inhibited by 35%, yet this result could not be validated statistically at the 95% level. As described in Albini et al. (2006), *FASEB J.*, 20, 527-529, the cells of a human Kaposi's sarcoma (KS-IMM) were transferred to immune-deficient mice and treated with approx. 1.2 mg/kg xanthohumol for 23 days; the growth of the tumor was inhibited by 68%.

The anti-mutagenic/anti-genotoxic studies by Miranda et al. (2000), *Cancer Lett.*, 149, 21-29; Dietz et al. (2005), *Chem Res. Taxieal.*, 18, 1296-1305; Plazar et al. (2007), *Mutat Res.*, 632, 1-8; Kac et al. (2008), *Phytomedicine.*, 15, 216-220 and Plazar et al. (2008), *Toxicol In Vitro*, 22, 318-327, describe anti-mutagenic and anti-genotoxic activities of xanthohumol. Cells in culture or rat liver are pre-incubated with xanthohumol and subsequently treated with genotoxic or cancer-generating substances that form radicals. Both, in the so-called Ames test, a test for mutagenic damage in bacterial culture, and in the Comet assay, a test that describes DNA damage caused by genotoxic substances, xanthohumol could inhibit damages up to 100%, depending on doses ranging between 0.01 to 10 μM.

Xanthohumol acts against microorganisms (Herath (2003), *Chem Pharm. Bull.* (Tokyo), 51, 1237-1240; Buckwold et al. (2004), *Antiviral Res.*, 61, 57-62; Wang (2004), *Antiviral Res.*, 64, 189-194; Frolich (2005), *J. Antimicrob. Chemother.*, 55, 883-887; Allen (2007), *Avian Dis.*, 51, 21-26). The studies by Miranda et al. (2000), *Drug Metab Dispos.*, 28, 1297-1302 and Frolich et al. (2005), *J. Antimicrob. Chemother.*, 55, 883-887 describe an effect against 4 different strains of plasmodiums generating malaria and the study by Allen (2007), *Avian Dis.*, 51, 21-26, gives a description of action against coccidian, a parasite that mainly colonises in the gastric-intestinal act of domestic animals. Xanthohumol acts in vitro as anti-viral against the HIV-1 (human immunodeficiency virus) (Wang et al. (2004), *Antiviral Res.*, 64, 189-194), against BVDV (bovine viral diarrhoea virus), HSV-1 and 2 (herpes simplex virus) and against CMV (cytamegalovirus) (Buckwold et al. (2004), *Antiviral Res.*, 61, 57-62).

The stability of the bones depends on equilibrium between bone-forming cells (osteoblasts) and bone-resorbing cells (osteoclasts). If the activity of the osteoclasts is proportionally greater, osteoporosis occurs. It was possible show in vitro that xanthohumol inhibits the resorption of bone by 35% in a concentration of 1 μM and by 94% with 10 μM (Tobe et al. (1997), *Biosci. Biotechnol. Biochem.*, 61, 158-159). Another study (Effenberger et al. (2005), *J. Steroid Biochem. Mol. Biol.*, 96, 387-399) describes the activation of osteoclasts.

Diacylglycerol acetyltransferase (DGAT) denotes an enzyme that is important for the formation and accumulation of triglycerides in the cell in the context of metabolic syndrome. The studies by Tabata et al. (1997), *Phytochemistry*, 46, 683-687 and Casaschi et al. (2004), *J Nutr.*, 134, 13401346, show an inhibition of this enzyme by xanthohumol in vitro; the study reported by Nozawa et al. (2005) *Biochem. Biophys. Res. Commun.*, 336, 754-761 was able to detect a reduction of triglycerides and of the plasma glucose level in mice.

Xanthohumol is poorly absorbed following oral application in the rat and remains largely unchanged in the excrement (Avula et al. (2004), *J Chromatogr. Sci.*, 42, 378-382; Stevens (2004), *Phytochemistry*, 65, 1317-1330; Hanske (2005), *Mol. Nutr. Food Res.*, 49, 868-873); in vitro it binds to cytosolic proteins (Pang et al. (2007), *Mol. Nutr. Food Res.*, 51, 872-879) resulting in glucuronidation in vitro (Yilmazer (2001), *FEBS Lett.*, 491, 252-256; Ruefer et al. (2005), *Mol. Nutr. Food Res.*, 49, 851-856; Kim et al. (2006), *J Nat Prod.*, 69, 1522-1524) and in vivo (Stevens (2004), *Phytochemistry*, 65, 1317-1330). The excrement featured a wide diversity of metabolites (Nookandeh et al. (2004), *Phytochemistry*, 65, 561-570), which, however, can also be derived from microbial activity in the intestine. The intestinal flora itself is not influenced in rats (Hanske et al. (2005), *Mol. Nutr. Food Res.*, 49, 868-873).

The oral application of xanthohumol in drinking water ($5 \times 10^{-4}$M ad libitum corresponding approximately to 28 mg/kg/day) for 4 weeks showed no unfavorable impact on the health of female C3H-mice. The development of weight and the appearance of the organs, the haematologically clinical parameters, the liver enzyme values and the parameter of glucose metabolism all remained uninfluenced by xanthohumol (Vanhoecke et al. (2005), In Vivo, 19, 103-107). In a study on rats, 100 mg/kg xanthohumol was administered daily for 4 weeks in drinking water, 500 mg/kg mixed into feed and 1000 mg/kg applied over pharyngeal tube. Except for a reduction in the weight of the liver due to the breakdown of glycogen in the high-dose groups (500 mg/kg/day and 1000 mg/kg/day) no toxic effects whatsoever could be determined (Hussong et al. (2005), *Mol. Nutr. Food Res.*, 49, 861-867). Since xanthohumol features anti-estrogen activity, investigation focused on whether reproduction with rats is impaired. The animals were treated for four weeks with 100 mg/kg/day xanthohumol in the drinking water and subsequently mated. Neither the pre-treatment of the female animals nor of the males had any influence on fertility or lactation (Hussong et al. (2005), *Mol. Nutr. Food Res.*, 49, 861-867).

It is remarkable how extremely multi-faceted the spectrum of activity of xanthohumol is. For example, it inhibits the mechanisms of carcinogenesis in the initiation phase and in the promotion and progression phases. Anti-oxidative and anti-inflammatory characteristics are just as important as the anti-estrogen activity, the inhibition of cellular proliferation, induction of apoptosis and the inhibition of angiogenesis. All these characteristics initially found in vitro, have now also been detected in vivo in animal experiments.

The studies on acute and subchronic toxicity (4 weeks) with up to 100 mg/kg/day per os gave no indication of toxicity in mice and rats. Glycogenolysis in the rat liver after daily doses in excess of 500 mg/kg xanthohumol can easily be explained by the significantly increased energy requirement culminating in the metabolism of large quantities of xenobiotics. It should be emphasized that such high concentrations are only administered to test possible toxicity. Recent studies presented cancer-preventing effects with doses of one-digit mg/kg.

Because the mechanisms of carcinogenesis in rodents and humans are comparable, since the metabolic effects of both are very similar and many studies are conducted with recombinant human enzymes, human cells in culture or with human cells in immune-deficient mice, similar results may also be anticipated for humans.

The invention described herein is based on the primary objective to provide means by which one, several or all of the health-promoting effects of xanthohumol on humans and/or animals can be enhanced.

Xanthohumol (hereinafter also referred to as XN), a prenylflavonoid (polyphenol) of hop, occurs in the lupulin glands of the hop cones. The content of XN in hops varies depending on the hop variety between 0.1 and 1%. The hop varieties having a high content of XN usually comprise a high portion of bitter substances.

Hop products may be divided in raw hops, hop pellets and hop extracts. Since XN occurs in the lupulin glands of the hop cone, hop pellets usually exhibit a high content of XN corresponding to the accumulation of alpha-acids. Hop extracts may be obtained by extraction with $CO_2$ and/or ethanol. Conventionally, XN enriched products are produced by a combination of both extraction methods. Depending on the production method XN contents of between 8 and 99% are achieved. The production of hop extracts enriched with XN and drinks comprising XN is described e.g. in the patents DE 19939350, DE 10256031, DE 10240065 and EP 1431385.

In the brewing process XN is relatively instable and is mainly precipitated via the trub, the yeast, by filtration and stabilization due to its limited solubility. Besides, XN is isomerized to iso-XN which also has a positive effect, however, to quite a lower extent compared to XN. With conventional methods less then 0.2 mg/l XN are reached in the final beer in most of the cases. In some stout or porter type dark beers XN contents of up to 1.2 mg/l XN were found (Walker et al., Brauwelt 2003). With a special brewing method which applies late hopping and a fast cooling of the beer wort it is possible to increase the XN content in non-filtered pale beers (DE 102 56 166).

Earlier in-house studies on behalf of the applicant, which focused on a technical field other than the subject-matter described herein, have shown that soluble roasted substances seem to be able to adsorb or bind XN and therefore apparently keep it in solution, which results in much higher yields of XN in hop extracts. In this context, a method has been provided for producing a roasted extract comprising XN from roasted products of cereals, cereal malt, coffee or cacao and a hop extract comprising XN. The hop extract comprising XN is characterized by a particularly high content of XN. Due to the use of this roasted extract, beers with a significantly increased content of XN compared to the prior art can be obtained in accordance with the German purity law, for instance (cf. EP 1 761 245 B1). Furthermore, the isomerisation of XN to iso-XN is suppressed to a large extent due to the improvement of the brewing method. Therefore, it is possible to increase dosage amounts of XN without allowing the beers to become unpleasantly bitter, for instance. Further, the addition of stabilizers is possible which would normally lead to a relevant decrease in the XN content.

While a high content of XN is also desirable in order to exploit the health-promoting effects of XN, it was first expected that the binding and/or adsorption of XN to the roasted substances would be detrimental to the beneficial activity of XN.

However, further subsequent studies directly comparing the activity of a XN containing roasted extract to the activity of pure XN now surprisingly showed that a composition containing a roasted extract and XN is even more effective than pure XN. Therefore, the interactions of the roasted substances with XN seem to not only facilitate a higher yield of XN in the extract, but furthermore they seem to enhance the beneficial activities of XN.

SUMMARY OF THE INVENTION

Therefore, the above primary objective is met by a composition, preferably pharmaceutical composition, comprising xanthohumol (XN), preferably in a therapeutically effective amount, for
(i) use in the treatment and/or prevention of cancer, and/or
(ii) use in the treatment and/or prevention of osteoporosis, and/or
(iii) use in the treatment and/or prevention of metabolic syndrome, and/or
(iv) use in the treatment and/or prevention of diabetes, and/or
(v) use in the treatment and/or prevention of cardiovascular disease(s), and/or
(vi) use as anti-oxidant, and/or
(vii) use as detoxifying agent, preferably as carcinogen detoxifying enzymes inducing agent, and/or
(viii) inhibiting metabolic activation of procarcinogenes, and/or
(ix) use as anti-mutagenic and/or anti-genotoxic agent, and/or
(x) use as anti-estrogenic and/or estrogenic agent, and/or
(xi) inducing apoptosis, and/or
(xii) use as anti-angiogenetic agent, and/or
(xiii) use as anti-inflammatory agent, and/or
(xiv) inhibiting NF-κB, and/or
(xv) use as antimicrobial agent, and/or
wherein the composition comprises or consists of (a) a roasted extract and (b) xanthohumol, preferably a hop extract comprising xanthohumol, and/or wherein the composition is obtainable or obtained by mixing (a) a roasted extract and (b) XN or, preferably, a hop extract comprising xanthohumol.

"Roasted extract" preferably denotes a cold or hot extract from coarsely ground or non-ground roasted malt or cereals including a hot or cold extract from coffee or cacao; "cereal malt" denotes a cereal that was artificially or controllably allowed to germinate.

"Hop extract comprising XN" preferably denotes an extract from hops which was obtained with the aid of a solvent and exhibits an, preferably increased, content of XN.

DETAILED DESCRIPTION OF THE PRESENT INVENTION

The above mentioned studies indicate that in combination with roasted substances, the beneficial effects of XN on human and/or animal health are synergistically enhanced.

Without wishing to be bound by theory, it is presently assumed that interactions between the roasted substances and XN increase the bioavailability of XN. On the one hand this means that more XN can be taken up by the body or a cell. On the other hand, an increased stability against metabolic degradation may play a role in the observed effects. As a result, smaller amounts of XN in the roasted extract exhibit higher activity compared to pure XN.

A composition according to the present invention is therefore ideally suited for the treatment and prevention of a diverse range of diseases.

For example, in the treatment and/or prevention of cancer, a composition according to the invention may interfere with tumor genesis, growth and/or proliferation by various interactions including anti-oxidant, anti-estrogenic or apoptosis-inducing as well as anti-angiogenetic activity. Enhanced detoxification of carcinogens and inhibition of metabolic activation of procarinogenes by a composition according to the invention as well as the anti-mutagenic and/or anti-genotoxic activity may advantageously serve to effectively prevent cancer.

Any of the above mentioned effects may at the same time be involved in the treatment and/or prevention of other disorders or diseases such as osteoporosis or metabolic syndrome.

Metabolic syndrome includes a wide range of disorders leading to severe diseases such as cardiovascular diseases and/or diabetes. Preventive measures as well as early treatment of metabolic syndrome are therefore highly desirable.

A composition according to the invention may also be applied for its anti-inflammatory action. Among the beneficial effects in this context, an efficient inhibition of NF-κB is observed and allows a use in the treatment and/or prevention of inflammatory events with glomerulonephritis, arteriosclerosis, septic shock, pulmonary fibrosis, asthma and/or rheumatoid arthritis.

Further advantages of a composition according to the invention are provided by the antimicrobial activity, including anti-viral, anti-bacterial as well as anti-parasitic effects.

In a preferred embodiment, a composition according to the invention has an XN content of at least 10 mg/kg, preferably of at least 20 mg/kg, preferably at least 50 mg/kg, in particular at least 200 mg/kg.

Preferably, the amount of roasted extract is sufficient to enhance, preferably to synergistically enhance, the above described therapeutic effect(s) of XN.

Due to the synergistic enhancement of the XN activity in a composition according to the invention, already low amounts of XN in the composition show beneficial effects but the content may be increased significantly if desirable since the above described toxicity test indicate a safe use.

The roasted extract in a composition according to the invention is preferably selected from the group consisting of a cold or hot extract of coarsely ground or non-ground roasted malt, cereals, coffee or cacao.

Preferably, for producing a roasted extract, a hot aqueous extract of the ground roasted products e.g. of barley, wheat, rye as well as the corresponding malts, coffee beans or cacao beans is prepared.

A composition according to the invention is preferably obtainable or obtained by a method comprising the step of mixing XN or, respectively, a hop extract comprising XN, with a roasted extract selected from the group consisting of a cold or hot extract from a coarsely ground or non-ground roasted malt, cereal, coffee or cacao.

The XN in a composition according to the invention may be provided synthetically, for example as described by Khupse and Erhardt in "Total synthesis of xanthohumol", *J Nat. Prod.*, 2007, 70(9), 1507-9, or it may be provided in an extract from hop.

Preferably, the hop extract comprising XN is added at the beginning of the heating period when preparing the roasted extract as the presence of the roasted products leads to a XN content which is by far higher than the solubility limit of XN in typical aqueous solutions.

In a preferred embodiment of the composition according to the invention, the used hop extract comprising XN has a content of XN which is in the range from 0.5 to 99% w/w (weight/weight percent) of XN.

The XN content in a composition according to the invention may be low as the beneficial effects are synergistically enhanced by the roasted substances in the roasted extract. Alternatively, a highly XN-enriched hop extract may be used and may be diluted strongly diluted in the resulting composition if convenient for the intended application.

In a further preferred embodiment, after mixing the hop extract comprising XN with the roasted extract, the resulting mixture is concentrated, preferably by evaporating, freeze drying or at reduced pressure, to dry matter of 40-50% w/w (weight/weight percent), particularly to 47 to 48% w/w (weight/weight percent).

Depending on the intended use, the mixture may be concentrated and subsequently diluted in a suitable medium.

The method by which a composition according to the invention is obtained or obtainable may further comprise the step of (pre-)dissolving the hop extract in ethanol for dissolving the XN, preferably by heating, agitating, mixing, shaking, supersonic treatment, the application of an alternating current and/or treatment with a dispersing means.

Any of the above mentioned treatments may serve to increase the amount of XN in solution facilitating the further processing and ensuring efficient interaction of a maximum amount XN with the roasted substances in the subsequent mixing with the roasted extract.

The present invention also relates to the use of a roasted extract for enhancing, preferably for synergistically enhancing, one or more therapeutic effect(s) of XN.

The therapeutic effects to be enhanced by the use according to the invention are preferably one, several or all of the effects selected from the group consisting of tumor-preventive effects, anti-oxidant effects, anti-tumor proliferation effects, carcinogen detoxification effects, anti-mutagenic effects, anti-genotoxic effects, inhibition of metabolic activation of procarcinogenes, anti-estrogenic effects, estrogenic effects, induction of apoptosis, anti-angiogenetic effects, anti-osteoporosis effects, anti-metabolic syndrome effects, anti-inflammatory effects, inhibition of NF-κB, anti-viral effects, anti-bacterial effects, anti-parasitic effects.

In a preferred embodiment of the use according to the invention, the XN is present in the form of or as a component of a hop extract.

In a further preferred embodiment of the use according to the invention, the roasted extract is selected from the group consisting of a cold or hot extract of coarsely ground or non-ground roasted malt, cereals, coffee or cacao.

In a particularly preferred embodiment of the use according to the invention, both, the roasted extract as well as the XN or, respectively, the hop extract, are components of a pharmaceutical composition.

For the use, wherein the roasted extract as well as the XN or, respectively, the hop extract, are components of a pharmaceutical composition, preferably the same effects and advantages are achieved as described above in the context of the use according to the invention.

The present invention further relates to a method for enhancing preferably for synergistically enhancing, one or more therapeutic effect(s) of XN, wherein the method comprises the following step:
  mixing XN with a roasted extract, the roasted extract being preferably selected from the group consisting of a cold or hot extract of coarsely ground or non-ground roasted malt, cereals, coffee or cacao,
with the proviso that the XN is pure XN, or synthetically produced XN and/or not derived from hop.

Pure XN may be either synthetically produced or purified from a hop extract excluding any potentially undesirable components which may interfere with the enhanced beneficial effects described herein and it may serve to avoid undesirable side-effects, which may result from the presence of other components.

The therapeutic effects to be enhanced by the method according to the invention are the same as mentioned in the context of the above described uses.

Furthermore, the present invention also relates to a method for producing a composition, preferably a pharmaceutical composition, wherein the method comprises the following step:
  mixing XN with a roasted extract, the roasted extract being preferably selected from the group consisting of a cold or hot extract of coarsely ground or non-ground roasted malt, cereals, coffee or cacao,
with the proviso that the XN is pure XN, or synthetically produced XN and/or not derived from hop.

For the method for producing a composition, preferably the same effects and advantages as detailed above apply.

Finally, the present invention also relates to a composition, preferably a pharmaceutical composition, consisting of or comprising a roasted extract, the roasted extract being preferably selected from the group consisting of a cold or hot extract of coarsely ground or non-ground roasted malt, cereals, coffee or cacao, and XN, with the proviso that the XN is pure XN, or synthetically produced XN and/or not derived from hop.

For the composition according to the invention, preferably the same effects and advantages as described in the context of the compositions, uses and methods detailed above apply.

It is apparent that a composition as described herein, in particular a pharmaceutical composition as described herein, may—depending on the intended use—contain one or more further components, such as conventional pharmaceutical additives, preferably one, two, three, or more pharmaceutically acceptable carriers, and/or diluents, and/or further ingredients, in particular one, two, three, or more pharmaceutical excipients.

Pharmaceutically acceptable ingredients may for example be binders such as natural or synthetic polymers, excipients, disintegrants, lubricants, surfactants, sweetening and other flavouring agents, coating materials, preservatives, dyes, thickeners, adjuvants, antimicrobial agents and carriers for the various formulation types.

Preferred pharmaceutical compositions according to the present invention are oral formulations and they may be solid formulations such as capsules, tablets, pills and troches, or a liquid suspension formulation; particularly preferred are gel tablets.

The pharmaceutical composition according to the invention may be used directly in the form of a syrup or gel or it may be combined with other pharmaceutically acceptable ingredients by mixing the components and optionally finely dividing them and/or filling them in capsules, composed for example from hard or soft gelatin and/or compressing tablets, pills or troches and/or suspending them in a liquid medium. Coatings may be applied after compression to form pills.

The present invention also relates to a method for the treatment and/or prevention of one, two or all of the diseases selected from the group consisting of cancer, metabolic syndrome, diabetes, cardiovascular disease(s) and osteoporosis comprising the step of administering to a subject in need thereof an effective amount of a pharmaceutical composition as described above.

In particular the present invention relates to a method for conferring one or more of the effects selected from the group consisting of tumor-preventive effects, anti-oxidant effects, anti-tumor proliferation effects, detoxification effects, anti-mutagenic effects, anti-genotoxic effects, inhibition of metabolic activation of procarcinogenes, anti-estrogenic effects, estrogenic effects, induction of apoptosis, anti-angiogenetic effects, anti-osteoporosis effects, anti-metabolic syndrome effects, anti-inflammatory effects, inhibition of NF-κB, anti-viral effects, anti-bacterial effects, anti-parasitic effects to a subject in need thereof, comprising the step of administering an effective amount of a pharmaceutical composition as described above to the subject.

For the methods for the treatment and/or prevention and the method for conferring the above listed effects preferably the same effects and advantages as described in the context of the compositions, uses and methods detailed above apply.

Example 1: Preparation of a Pharmaceutical Composition for Medical Purposes as Described Herein After mashing of malt comprising 1.9 kg of roasted barley malt (Carafa™, type 2, Fa. Weyermann, Bamberg) and 0.1 kg of Pilsen type malt according to the congress method and mash separation, 25 g/l of a hop extract enriched with XN are added (XanthoExtrakt, Simon H. Steiner Hopfen GmbH, XN 2.0%) during boiling of the roasted malt. After separation of hot trub and a separation with diatomaceous earth the roasted malt comprising XN is concentrated in vacuo (200 mbar, ca. 55 [deg.] C.) to an extract content of approximately 50% w/w. The syrup like extract ("density 1.25" kg/l) has a content of XN of approximately 1320 mg/kg. The roasted malt extract containing XN can directly be mixed with any conventional pharmaceutical carriers and additives as desired.

What is claimed is:

1. A method of administering an effective amount of the combination of xanthohumol (XN) and a roasted extract to a subject in need thereof so as to enhance one or more therapeutic effects of XN, wherein said one or more therapeutic effects comprise the treatment and/or prevention of one or more of a cardiovascular disease, cancer, osteoporosis, metabolic syndrome and an infection.

2. The method of claim 1, wherein the one or more therapeutic effects comprise the treatment and/or prevention of cardiovascular diseases.

3. The method of claim 1, wherein the one or more therapeutic effects comprise the treatment and/or prevention of cancer.

4. The method of claim 1, wherein the one or more therapeutic effects comprise the treatment and/or prevention of osteoporosis.

5. The method of claim 1, wherein the one or more therapeutic effects comprise the treatment and/or prevention of metabolic syndrome.

6. The method of claim 1, wherein the one or more therapeutic effects comprise the treatment and/or prevention of infections.

7. The method of claim 1, wherein a resultant composition comprises at least 20 mg of XN per kg of the resultant composition.

8. The method of claim 1, wherein a resultant composition comprises at least 50 mg of XN per kg of the resultant composition.

9. The method of claim 1, wherein a resultant composition comprises at least 200 mg of XN per kg of the resultant composition.

10. The method of claim 1, wherein the one or more therapeutic effects comprise the treatment of one or more of a cardiovascular disease, cancer, osteoporosis, metabolic syndrome and an infection.

11. The method of claim 10, wherein the roasted extract is selected from cold or hot extracts of coarsely ground or non-ground roasted malt, cereals, coffee or cacao.

12. The method of claim 10, wherein the one or more therapeutic effects comprise the treatment of a cardiovascular disease.

13. The method of claim 10, wherein the roasted extract comprises an extract of roasted malt.

14. The method of claim 1, wherein the XN is present as a component of a hop extract.

15. The method of claim 14, wherein the hop extract comprises from 0.5% to 99% w/w of XN.

16. The method of claim 15, wherein after combining the hop extract comprising XN with the roasted extract a resultant mixture is concentrated to a dry matter content of from 47 to 48% w/w.

17. The method of claim 14, wherein after combining the hop extract comprising XN with the roasted extract a resultant mixture is concentrated to a dry matter content of from 40 to 50% w/w.

18. The method of claim 1, wherein the roasted extract is selected from cold or hot extracts of coarsely ground or non-ground roasted malt, cereals, coffee or cacao.

19. The method of claim 18, wherein the roasted extract comprises an extract of roasted malt.

20. The method of claim 19, wherein after combining the hop extract comprising XN with the roasted extract a resultant mixture is concentrated to a dry matter content of from 47 to 48% w/w.

* * * * *